United States Patent [19]

Anderson et al.

[11] 4,439,211
[45] Mar. 27, 1984

[54] SUPPRESSION OF FOOD DUSTS AND THE LIKE

[75] Inventors: Donald E. Anderson, Maumee; Glenn E. Hall, Toledo; Kevin M. Foley, Maumee, all of Ohio

[73] Assignee: The Andersons, Maumee, Ohio

[21] Appl. No.: 343,729

[22] Filed: Jan. 29, 1982

Related U.S. Application Data

[63] Continuation-in-part of Ser. No. 302,729, Sep. 16, 1981, abandoned.

[51] Int. Cl.³ .............................................. B01D 50/00
[52] U.S. Cl. ....................................... 55/1; 55/385 R; 55/430; 426/455; 241/31; 193/11
[58] Field of Search .......................... 55/1, 385 R, 430; 426/507, 455, 622; 193/11; 169/64, 65; 134/25.1, 25.3; 141/69, 70; 241/31, 15

[56] References Cited

U.S. PATENT DOCUMENTS 3,549,336 12/1970 Hodel .................................. 23/313 R
3,684,526 8/1972 Lowery ................................. 426/455
3,939,881 2/1976 Scott .................................... 55/385 R

FOREIGN PATENT DOCUMENTS 2042866 10/1980 United Kingdom .................. 241/31

OTHER PUBLICATIONS

Pyler-Baking Science & Technology published by Siekel Publishing Co., Chicago, Illinois, 2/74, pp. 309, 343, 344, 346, 347.

Primary Examiner—Bernard Nozick
Attorney, Agent, or Firm—Emch, Schaffer & Schaub

[57] ABSTRACT

A method of reducing the liberation of dust particles from a dry particulate matter is disclosed. The particulate matter is transferred to a location where it falls through the air, a small amount of water is introduced onto the particles of material in the material stream, the water being added in the amount of at least 1.01 % and no more than 1% of the weight of the dry particulate matter. The wetted particles contact each other and are distributed generally uniformally throughout the remainder of the material. The delivery of the wetted particles is delayed by a period of at least one second. A smooth path is provided for the material stream after the uniform distribution and prior to discharge at the discharge location.

24 Claims, 19 Drawing Figures

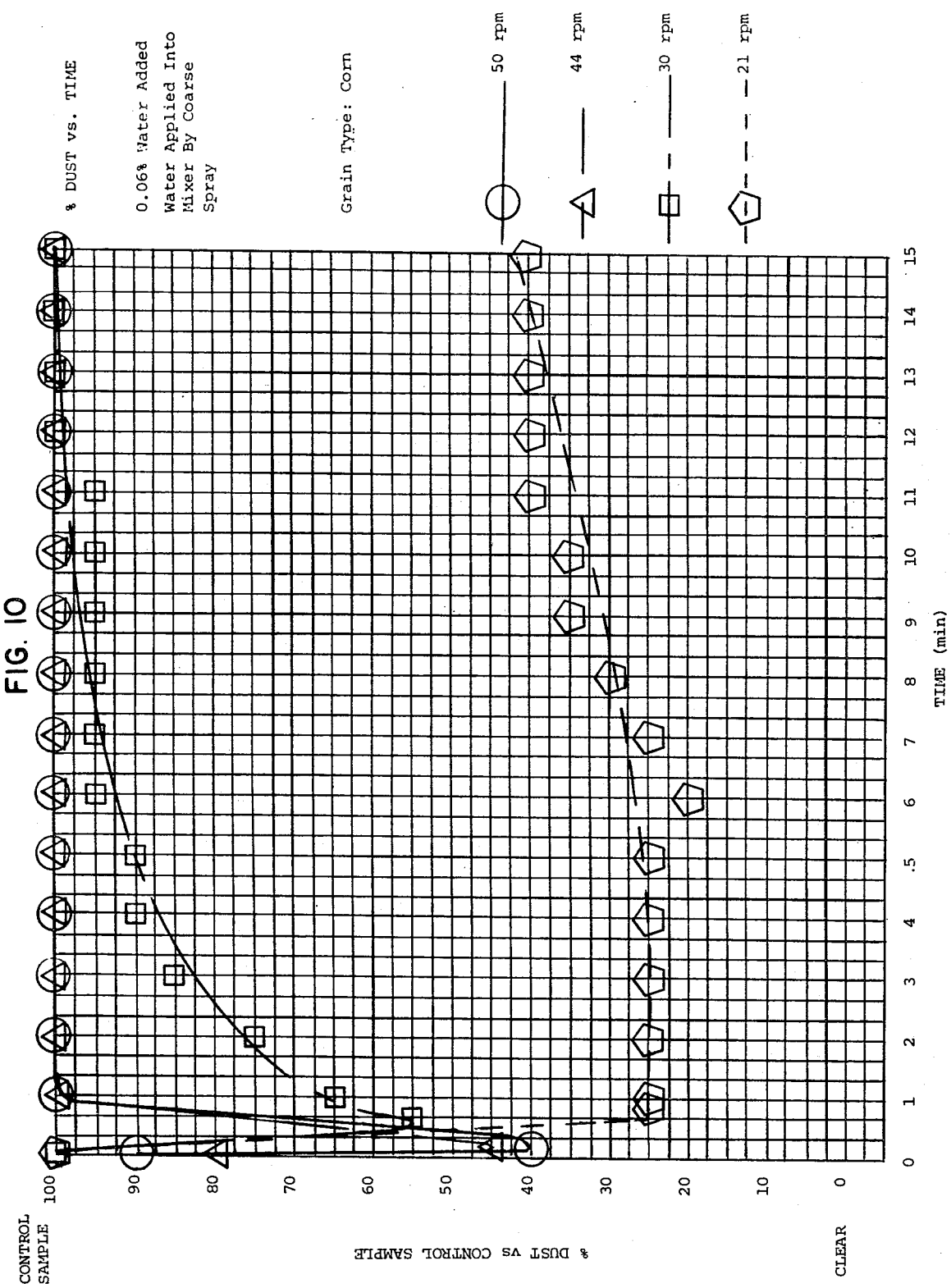

Schematic Diagram of Liquid Application Locations

FIG. 14

EXAMPLES FROM FULL SCALE WORK WITH CORN

| Test No. | Liquid Added | | | Loading Mode | Liquid Applied % | Air Opacity % | Grain Flow Rate Bushels/Hr. | Point Of Liquid Addition |
|---|---|---|---|---|---|---|---|---|
| | Water % | Oil % | Emulsifying Agent* % | | | | | |
| 1 | 0 | 0 | 0 | A or B | 0 | 31 | 20,500 | - |
| 2 | 100 | 0 | 0 | A | 1.0 | 31 | 20,500 | D |
| 3 | 100 | 0 | 0 | B | 0.35 | 31 | 20,500 | C |
| 4 | 100 | 0 | 0 | A | 0.35 | 6 | 20,500 | C |
| 5 | 100 | 0 | 0 | A | 0.21 | 8 | 20,500 | C |
| 6 | 100 | 0 | 0 | A | 0.10 | 19 | 20,500 | C |
| 7 | 100 | 0 | 0 | A | 0.05 | 25 | 20,500 | C |
| 8 | 100 | 0 | 0 | A | 0.02 | 28 | 20,500 | C |
| 9 | 100 | 0 | 0 | A | 0.01 | 28 | 20,500 | C |
| 10 | 100 | 0 | 0.05 | A | 0.35 | 11 | 20,500 | C |
| 11 | 100 | 0 | 0.05 | A | 0.21 | 12 | 20,500 | C |
| 12 | 100 | 0 | 0.05 | A | 0.10 | 18 | 20,500 | C |
| 13 | 100 | 0 | 0.05 | A | 0.05 | 22 | 20,500 | C |
| 14 | 100 | 0 | 0.05 | A | 0.02 | 23 | 20,500 | C |
| 15 | 100 | 0 | 0.05 | A | 0.01 | 28 | 20,500 | C |
| 16 | 99 | 1 | 0.05 | A | 0.35 | 8 | 20,500 | C |
| 17 | 99 | 1 | 0.05 | A | 0.21 | 11 | 20,500 | C |
| 18 | 99 | 1 | 0.05 | A | 0.10 | 16 | 20,500 | C |
| 19 | 99 | 1 | 0.05 | A | 0.05 | 22 | 20,500 | C |
| 20 | 99 | 1 | 0.05 | A | 0.02 | 28 | 20,500 | C |
| 21 | 99 | 1 | 0.05 | A | 0.01 | 28 | 20,500 | C |
| 22 | 90 | 10 | 0.05 | A | 0.34 | 8 | 20,500 | C |
| 23 | 90 | 10 | 0.05 | A | 0.21 | 10 | 20,500 | C |
| 24 | 90 | 10 | 0.05 | A | 0.10 | 14 | 20,500 | C |
| 25 | 90 | 10 | 0.05 | A | 0.05 | 19 | 20,500 | C |
| 26 | 90 | 10 | 0.05 | A | 0.02 | 25 | 20,500 | C |
| 27 | 90 | 10 | 0.05 | A | 0.01 | 26 | 20,500 | C |
| 28 | 54 | 46 | 0.05 | A | 0.33 | 11 | 20,500 | C |
| 29 | 54 | 46 | 0.05 | A | 0.20 | 15 | 20,500 | C |
| 30 | 54 | 46 | 0.05 | A | 0.09 | 21 | 20,500 | C |
| 31 | 54 | 46 | 0.05 | A | 0.04 | 24 | 20,500 | C |
| 32 | 54 | 46 | 0.05 | A | 0.02 | 25 | 20,500 | C |
| 33 | 54 | 46 | 0.05 | A | 0.01 | 22 | 20,500 | C |

*Polysorbate 80 obtained from Durkee Foods.

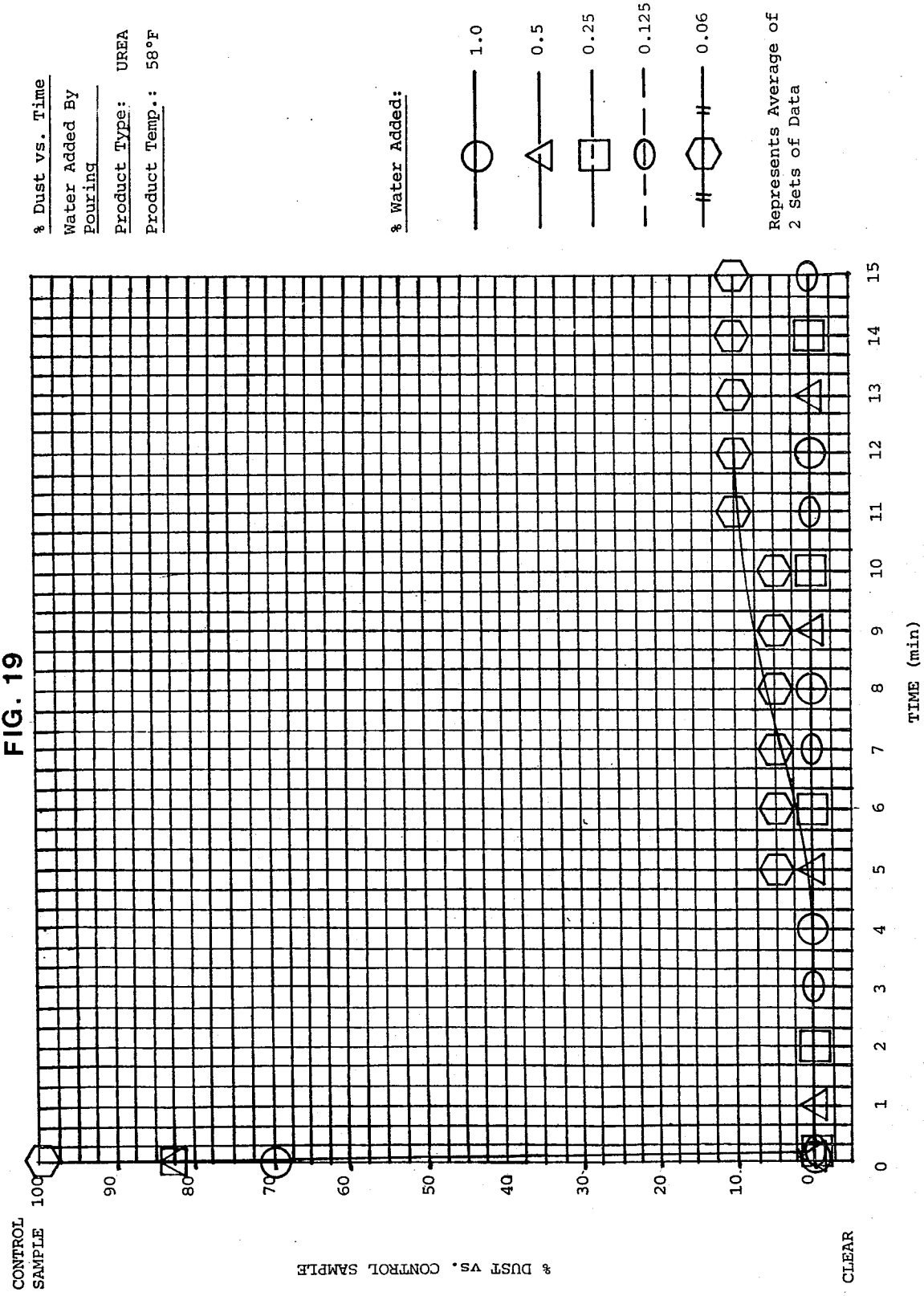

SUPPRESSION OF FOOD DUSTS AND THE LIKE

This patent application is a continuation-in-part patent application of patent application Ser. No. 302,729, filed Sept. 16, 1981, which is now abandoned.

TECHNICAL FIELD

The present invention relates to the material handling of particulate perishable foods; and more particularly to the material handling of grain.

BACKGROUND OF THE INVENTION

It has been virtually heretofore to transport or refine dry organic foods without producing dust size particles thereof. These dusts when mixed with air are troublesome to man and animals; and in proper concentrations can be explosive. This is true of all grains, the milled products thereof, as well as processed foods made therefrom. Dried milk, sugars, powdered eggs, starches, and protein meals are further examples of materials that produce troublesome dusts. The problems that arise from grain dusts are well known, and these problems have existed since the time man first started threshing grain and storing the kernels thereof in a dry form for future use. Man has long known that if he wets the grain with water, that he can reduce the liberation of dust to the air; but the problem with wetting grain is that it can not be stored thereafter without spoiling. When grain has been wetted heretofore, it has been necessary to use it up before it mildewed and spoiled, or to dry it immediately so that it could be stored. Man has also known that oils of one kind or another can be sprayed on dusty materials to keep down the dust. In most cases oils, and particularly edible oils, can become rancid and may leave taste and/or odors on the food. In the handling of coal, streams of water are used to impinge upon the dust and carry it away, or the streams are used to wash the coal and extract the dust size particles therefrom. It can be seen that the conventional methods for controlling dust in nonfood items are not applicable for the control of dust in food products.

From all of the conventional knowledge of controlling dust, only conventional electrical and mechanical dust collecting equipment has been adapted for the control of food dusts. Such equipment is large and expensive and it is not always practical to run air ducts to every location were food dust may arise. Obviously the problem of controlling food dusts is more complicated than that involved in handling inorganic dusts. The problem is almost as old as modern man; and yet, the problem exists to this day.

It is therefore an object of the present invention to provide a new and improved method of controlling food dusts which is reliable, and inexpensive, and does not produce spoilage, unsanitary build-ups, or explosion hazards in any way.

For those who, after reading the solution to this problem, may say that some of the steps involved are obvious to them, let us remind the reader that there are very good reasons which have caused man not to use some of the steps involved; and that prior to applicants' work no one knew the narrow limits within which some of the other steps could be safely undertaken.

Still other objects and advantages of the invention will become apparent to those skilled in the art to which the invention relates after reading the following description taken with the accompanying drawings.

BRIEF DESCRIPTION OF THE DRAWINGS

FIG. 10 is a graph showing the reduction in dust achieved in the equipment of FIGS. 11 and 12 when 0.06% by weight water is added in the form of a coarse spray using a variety of mixer RPMs.

FIG. 14 is a table of data obtained from tests made in the facility depicted in FIG. 13.

FIG. 19 is a graph showing the levels of fertilizer dust achieved when a mixer of FIGS. 11 and 12 was charged with urea fertilizer and water was poured therein.

DESCRIPTION OF THE PREFERRED EMBODIMENTS

According to the present invention we have discovered what appears to be a new and improved process for greatly surpressing the escape of dust from particulate materials. In the process, applicants utilize a very small amount of water, so small an amount that it can be left in food without causing it to spoil. In practicing the process, certain time constraints must be conformed to. First, there is a time delay after the particles are dampened, before it becomes effective. Secondly, there appears to be a time during which the particles must remain consolidated before it becomes most effective. Thirdly, in most applications there is a limited time period thereafter during which it is most effective and during which the materials should be dumped, or subjected to whatever step normally liberated the dust. During the second period of time, it appears best to keep the food consolidated. The process will now be explained as it is applied to various food handling equipment.

A very serious dust problem occurs at the exit of chutes where food is allowed to free fall through air over considerable distances. Spraying water on the food at such locations where it free falls does very little, if any, good in preventing the escape of the dust into the air. The present invention was applied to such a situation wherein approximately 20,000 bushels per hour of shelled corn, soybeans and wheat were outloaded from an elevator by a steel chute into a container ten or more feet below. The chute was modified to spray water droplets at both sides of the stream of corn, soybeans or wheat as it traversed a short free fall within the chute where the stream thinned out appreciably. After the free fall, the kernals were consolidated into a more narrow deeper region of the chute where it was confined for approximately 3 seconds before reaching the end of the chute. The chute was uncoated steel. The installation is depicted schematically in FIG. 1 of the drawings. By actual tests it was shown that water droplets amounting to no more than 0.05% by weight of corn, reduced the opacity of the air in the container from 28% to an acceptable level of 20%. (Opacity is a measure of the reduction in light that is transmitted through an environment.) When 0.1% of water droplets were applied, an opacity in the dusty air of 33% was reduced to 20%; and when 0.2% was applied to the corn an opacity of 43% was reduced to 20%. The corn that was fed to the chute had an initial moisture content of 14%. It was found that the moisture added absorbed into the corn without damage and without leaving surface areas where mildew or spoilage developed. All three levels can bring an untreated dust having an opacity of 12% to a level of approximately 4%.

This discovery and demonstration now makes it possible to change the approach to the handling and transporting of foods. Henceforth it will be possible to ascertain what the moisture level of the perishable food is, and then transport it through a number of dust generating steps at each of which a controlled amount of moisture could be added. At any large grain handling facility, for example, there may be some flow paths to some storage areas having only one dust liberating location which needs to be controlled. Paths to other storage areas may have two or more successive locations which need dust control. At each dust liberating location, it can be determined what percentage of water needs to be added to control its dust. By knowing the incoming moisture, the operator can determine to what area the grain can be sent without drying and can determine how much drying is necessary to send the grain to other areas. He can then route the grain through a drier, if necessary, to bring the moisture level down to a level which will accommodate the moisture that is needed to be added for the route selected.

In this regard, applicants have made another discovery. Applicants have discovered that if the added water is caused to contain more than approximately 0.5 ppm of available chlorine, the normal limits of moisture content for storage can be pushed or exceeded without developing mildew.

The discoveries of the present invention are adaptable to all of the conventional machinery used in the material handling of dry solid foods. FIG. 1 of the drawings shows how grain spouts would be altered to utilize the principles of the present invention. At a point upstream of the end of the spout, a water mixing area would be installed. A preferred method of mixing is to provide a short free fall area, where the stream of material thins out and the particles thereof move out of engagement with each other. Sprays of water are directed at opposite sides of the falling material to apply the predetermined amount of water which is to be added. Applicants find that large size water proplets can give better results than fine mists. Large size droplets are better able to carry into the stream of falling grain. Also it appears to be not necessary to coat each particle of grain, since during the consolidation step which follows, the wetted grain kernels will abut unwetted grain kernels to provide a transfer of moisture. Also it appears that a thicker film of surface moisture can more quickly surround dust particles that are pushed into or are attracted to the surface of the water during the consolidation step. Thorough and complete wetting of the kernels does not appear essential before the consolidation step.

The mixing location would be chosen to give several seconds delay as determined by the length of time for the kernels to move from the mixing area to the end of the spout. After consolidation as little agitation as possible should be had before the kernels reach the end of the spout. Unnecessary mixing during this time appears to increase dust.

FIG. 2 of the drawings shows how a conventional belt conveyor can be modified to incorporate the principles of the present invention. A mixing zone is provided upstream of the discharge end of the conveyor by providing a reverse loop in the top flight of the conveyor. The reverse loop is such as to provide a short free fall, and spray nozzles are installed to inject the desired amount of water into the free falling stream of particles from opposite sides thereof. A standard belt transfer point would offer a similar opportunity to add water. Here again, the distance of the mixing area from the discharge end of the conveyor is determined by the speed of the conveyor, the material being handled by the conveyor, as well as the amount of water that can be added, and the violence which occurs at the discharge end of the conveyor. Further information concerning time periods will be given later.

FIG. 3 of the drawings shows how a conventional bucket elevator installation could be altered to utilize the principles of the present invention. The food being fed to the boot of the elevator is caused to free fall, and sprays are directed at opposite sides of the free falling material. In this equipment, consolidation occurs in the boot as well as in the buckets. Dust is usually liberated at the top of the elevator where the buckets are discharged, but in this instance, very little dust will be generated.

FIG. 4 of the drawings shows how a conventional auger conveyor installation would be altered to utilize the principles of the present invention. The auger conveyor would be run fast enough so that about half of the auger is exposed, to insure adequate mixing. A water spray is added to the exposed surface of the food therein, at a location to provide the necessary time lapse for mixing the water throughout. The location of the spray should be such that the water added is not completely absorbed into the food before it is discharged from the conveyor.

EXAMPLES FROM SMALL SCALE WORK

Figure 1:
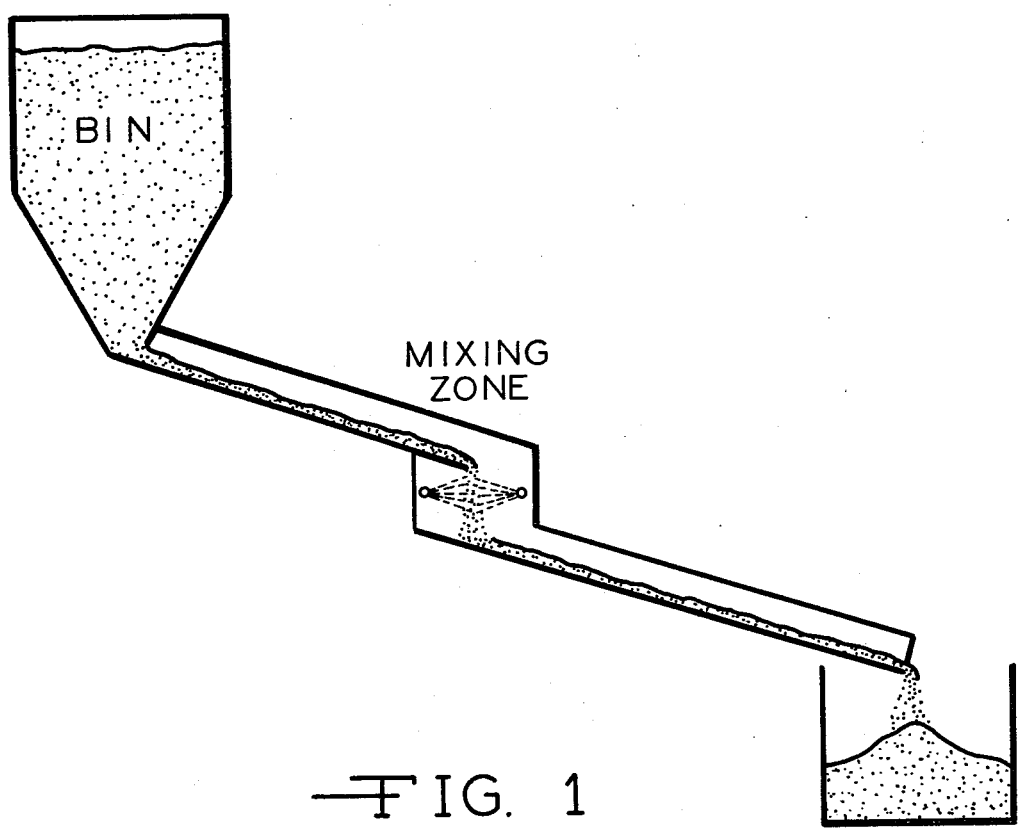
FIG. 1 is a schematic elevational view of a chute arrangement adapted to utilize the present invention.
Figure 2:
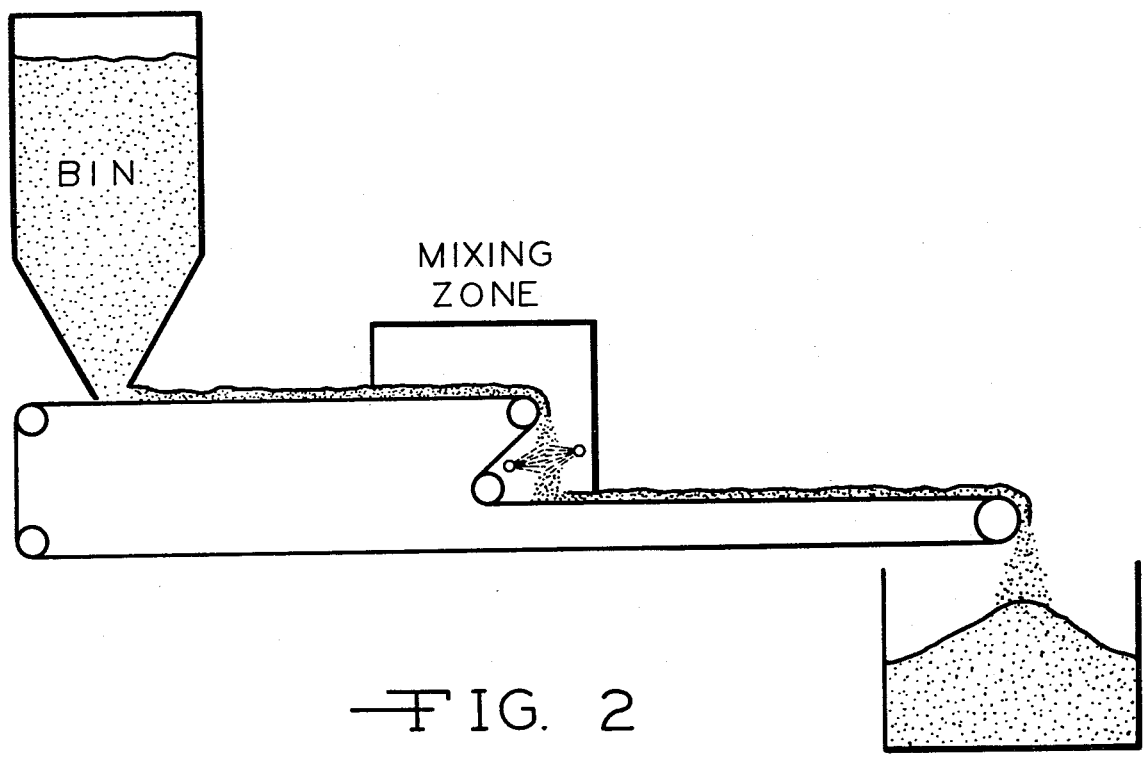
FIG. 2 is a schematic elevational view of a conevyor arrangement adapted to utilize the present invention.
Figure 3:
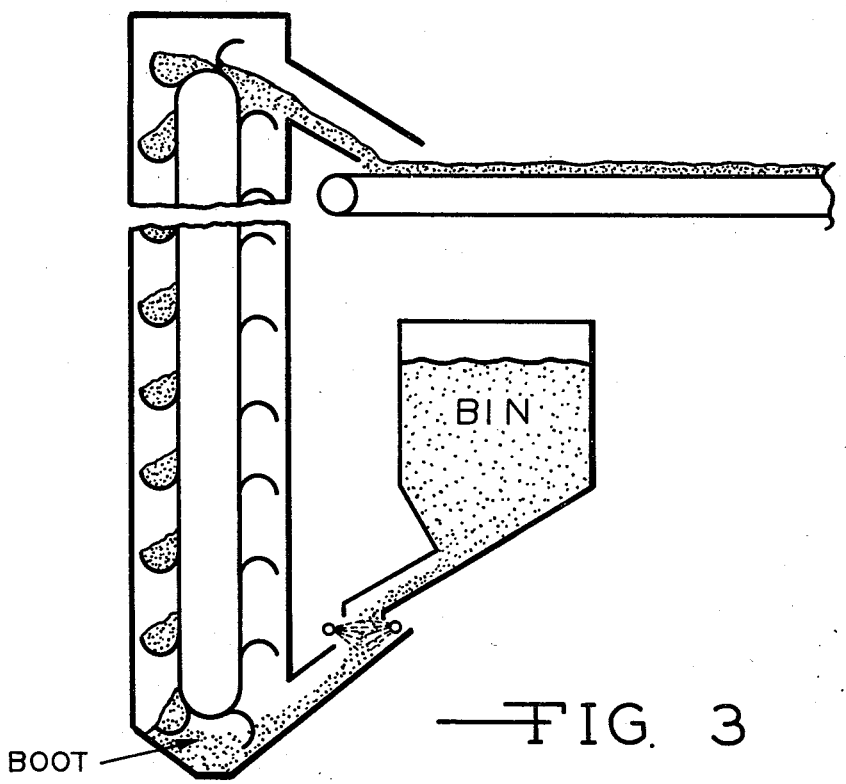
FIG. 3 is a schematic elevational view of a bucket elevator arrangement adapted to utilize the present invention.
Figure 4:
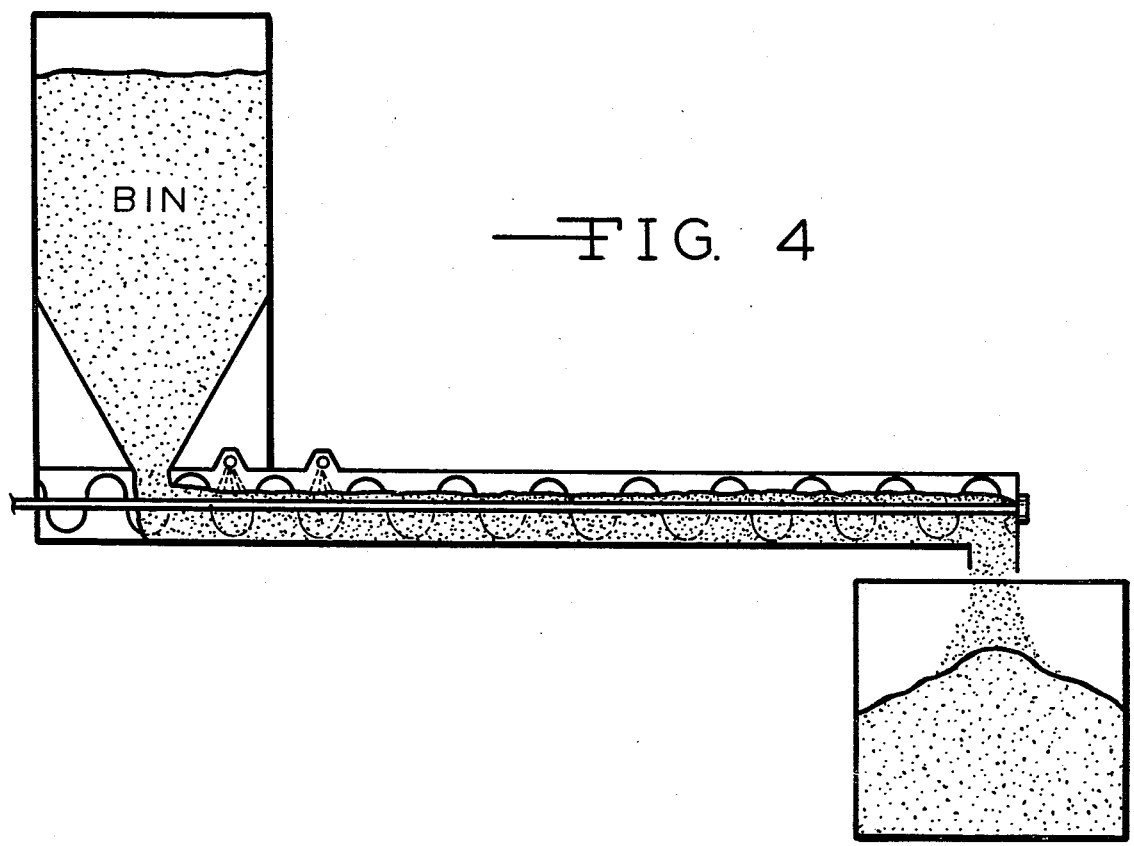
FIG. 4 is a schematic elevational view of an auger conveyor arrangement adapted to utilize the present invention.
Figure 5:
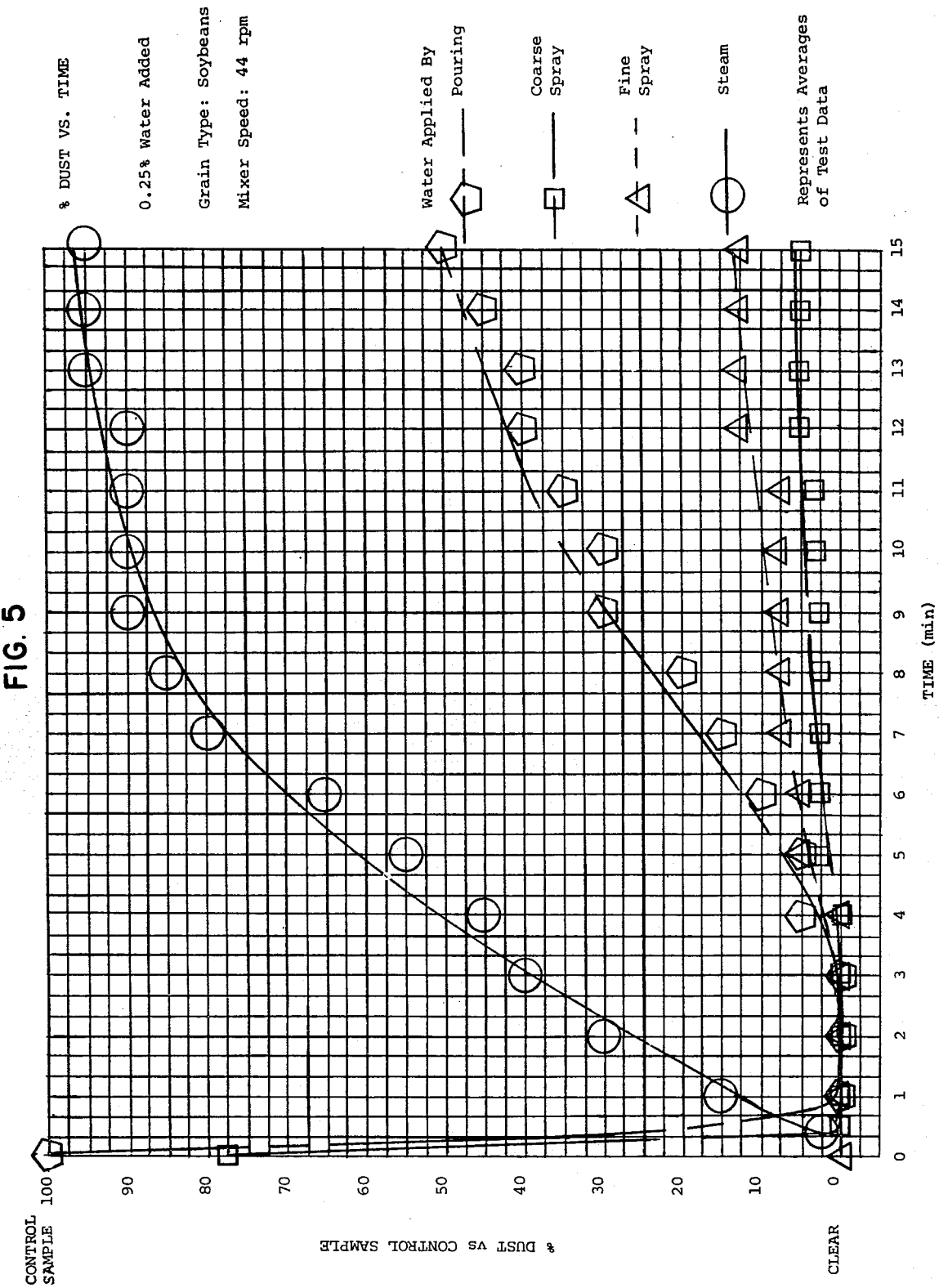
FIG. 5 is a graph showing the reduction in dust achieved in the equipment of FIGS. 11 and 12 when water is applied by pouring, coarse spray, fine spray and steam.
Figure 6:
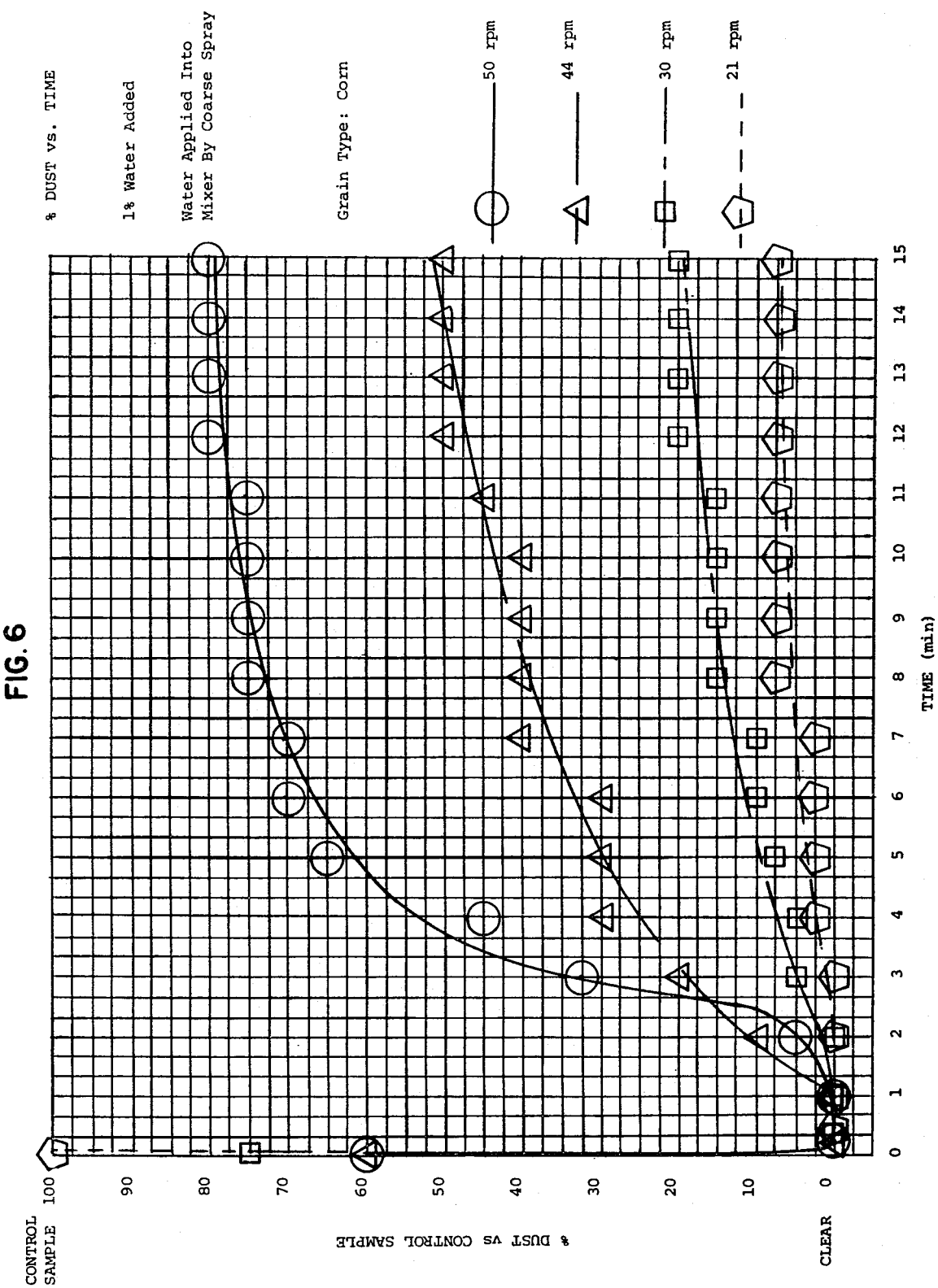
FIG. 6 is a graph showing the reduction in dust achieved in the equipment of FIGS. 11 and 12 when 1% by weight water is added in the form of a coarse spray using a variety of mixer RPMs.
Figure 7:
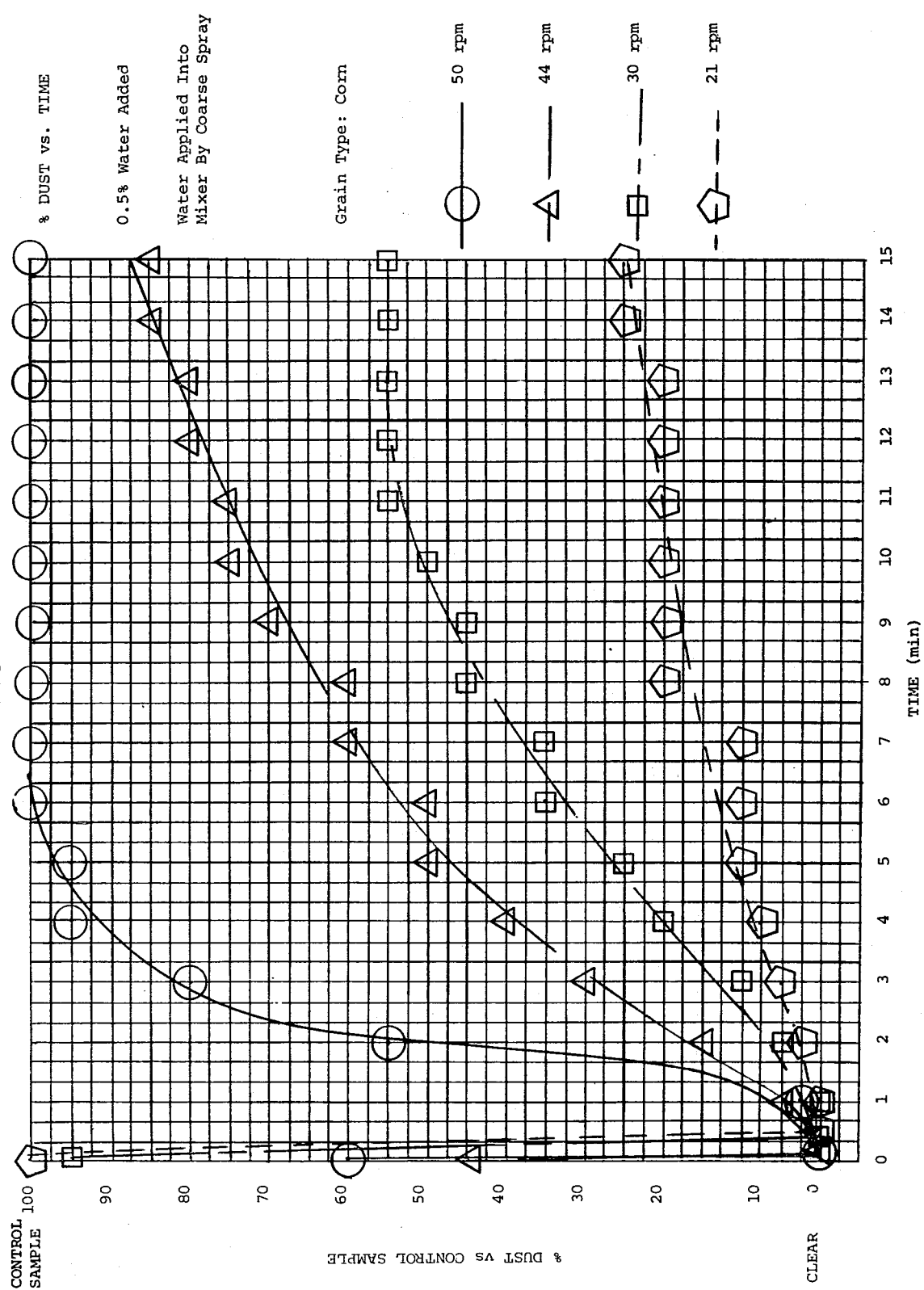
FIG. 7 is a graph showing the reduction in dust achieved in the equipment of FIGS. 11 and 12 when 0.5% by weight water is added in the form of a coarse spray using a variety of mixer RPMs.
Figure 8:
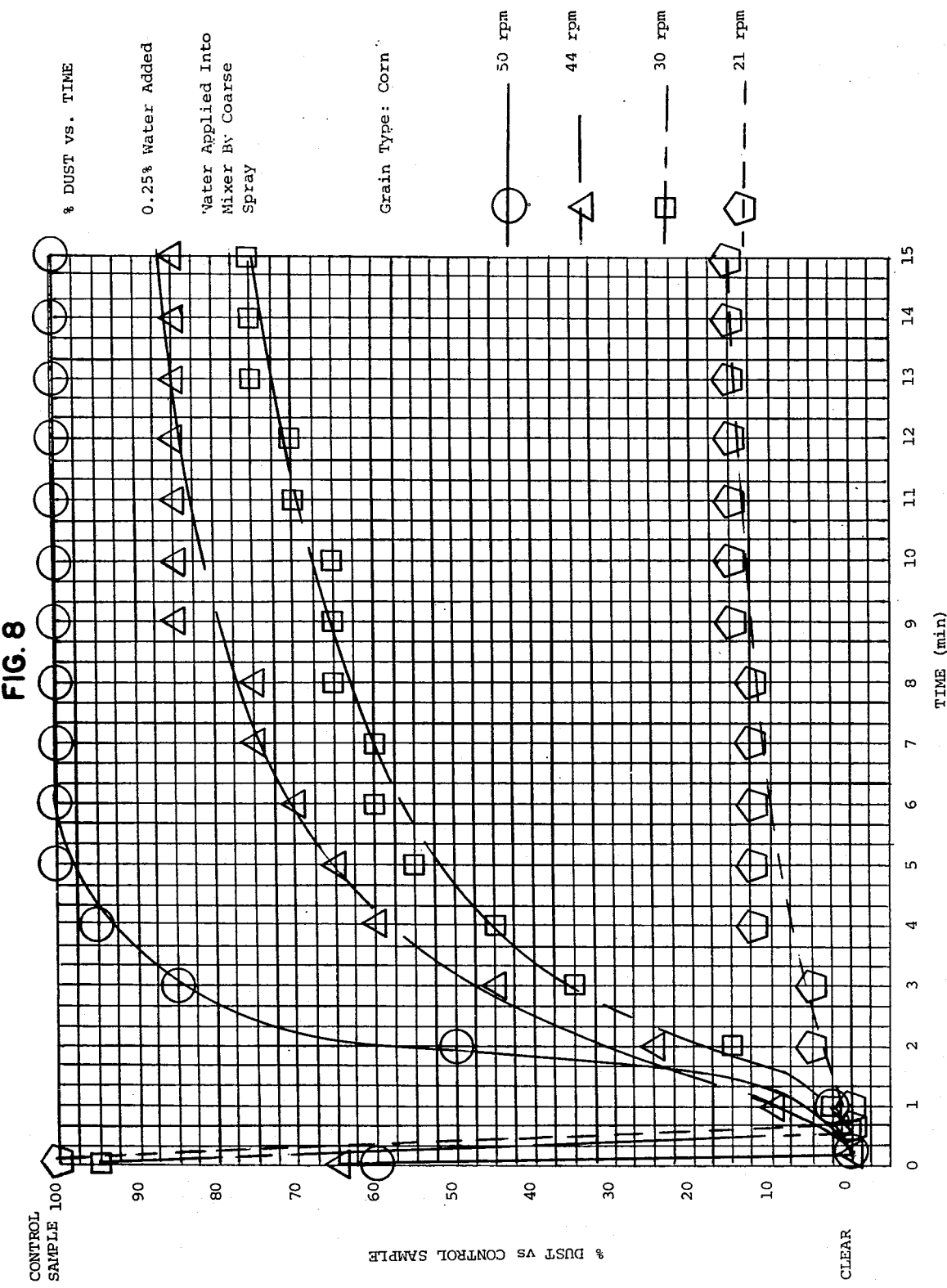
FIG. 8 is a graph showing the reduction in dust achieved in the equipment of FIGS. 11 and 12 when 0.25% by weight water is added in the form of a coarse spray using a variety of mixer RPMs.
Figure 9:
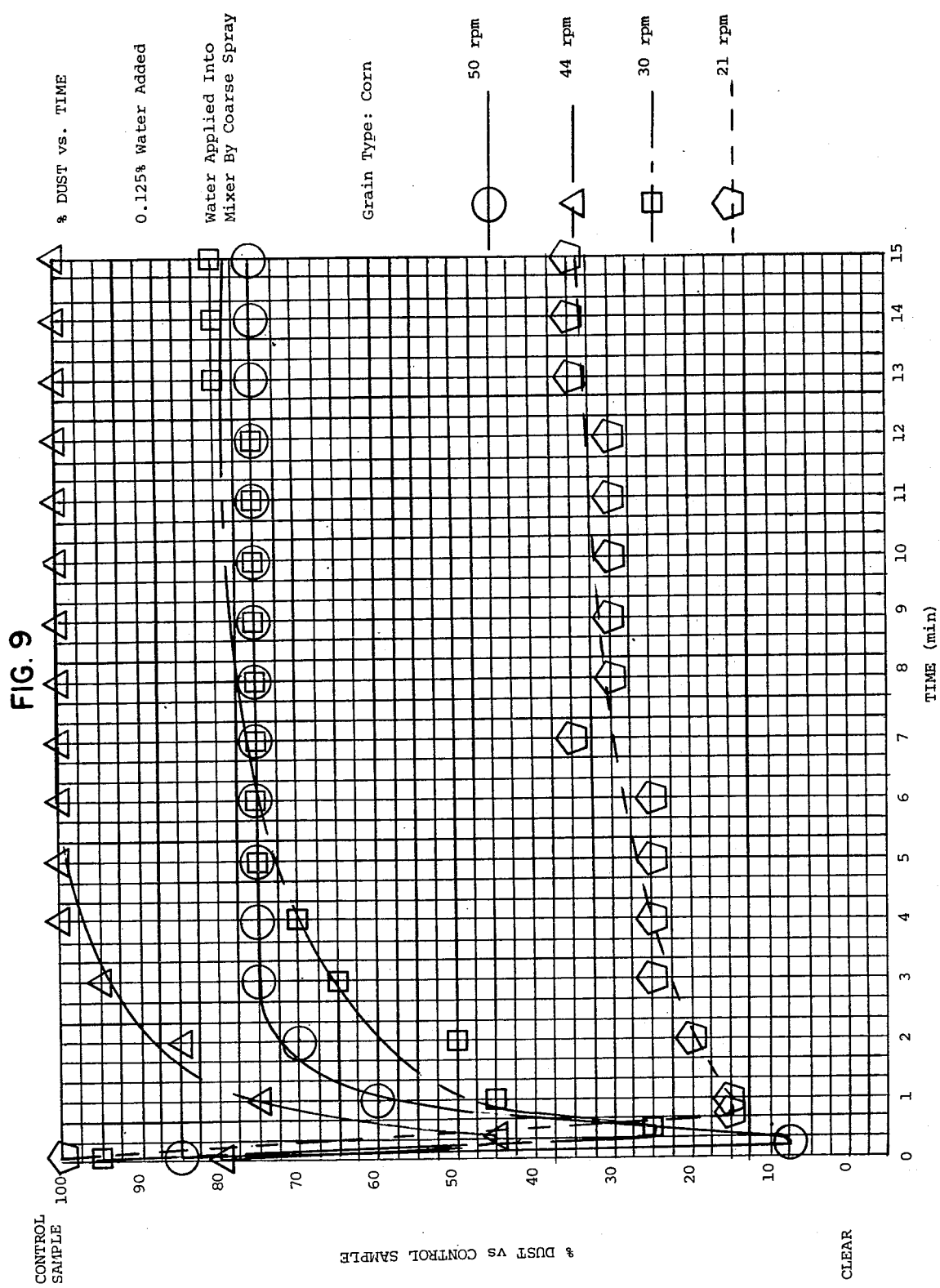
FIG. 9 is a graph showing the reduction in dust achieved in the equipment of FIGS. 11 and 12 when 0.125% by weight water is added in the form of a coarse spray using a variety of mixer RPMs.

A number of experiments were conducted to ascertain the affect of water droplet size, as well as the speed of response, and duration of effectiveness of different concentrations of water. To do this, two small identical commercial cement mixers were fitted with covers over their open ends. The covers had small centrally located openings through which the water could be sprayed or dumped. One cement mixer was used as a control, and the other was used to observe the effect of the water. The mixers were rotated at 44 RPM, identical amounts of grain were added to each mixer and the mixers were rotated until the dust level in each reached equilibrium. Thereafter, a known amount of water was added into one of the mixers and the dust level checked against the control at recorded periods of time. The experiments were repeated using different amounts of water, different nozzles to give different size particles, and steam. As shown in FIG. 5, water sprayed into the mixer controlled dust for a longer period of time than water poured into the mixer which in turn was more effective than steam. The experiments were repeated at 50 RPM, at 30 RPM and at 21 RPM, using a coarse spray, and the data derived as illustrated in FIGS. 6 through 10 for various water levels.

Figure 12:
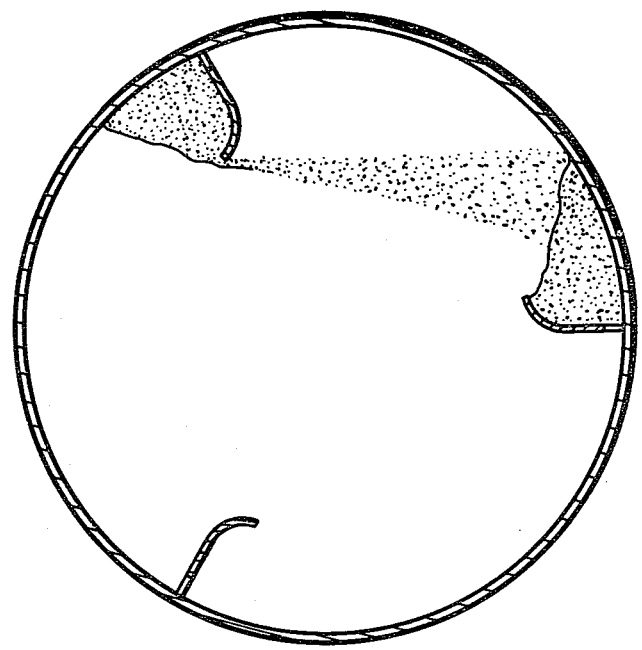
FIG. 12 is a sectional view taken approximately on the line 12—12 of FIG. 11.
Figure 11:
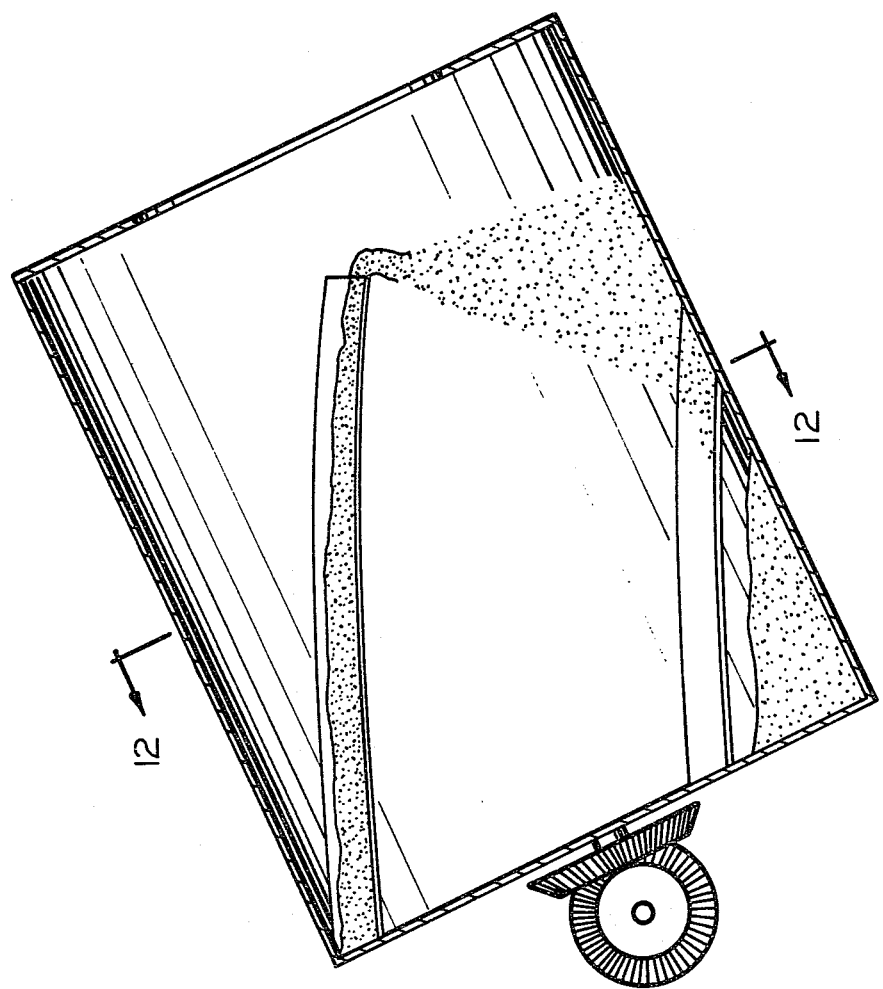
FIG. 11 is a schematic side elevational view, partly in section, of a cement mixer arrangement used to generate dust.

FIGS. 11 and 12 are schematic drawings showing the configuration of the mixers used. It will be seen, that each had three equally spaced apart blades that were fixed to the sides of the mixer drum. The blades had upwardly turned inner edges to retain a depth of material thereon and they were spaced approximately one half inch away from the drum to allow some material to flow down along the drum as the blades were rotated up out of the material lying along the bottom of the drum. In every instance, the dust level in the mixer fell after the water was added. Generally, it appears that the dust level dropped at a rate generally proportional to the speed of the mixer until a minimum plateau was reached. Thereafter, the dust level would stay generally constant for a bit and would then rise. The amount of rise appears to be governed by two factors: first, the violence of agitation; and secondly, the time for the free water to be absorbed into the grain.

When the mixers were run at 50 RPM, the dust level, compared to the control, recovered most rapidly. It is theorized that the rapid mixing quickly spreads the water more uniformly throughout the grain causing it to be absorbed more readily into the grain. It now appears that water vapor surrounding the grain has a very low order of effect compared to liquid water on the surface of the grain, albeit that the liquid is even a monomolecular layer. At the 21 RPM speed, the dust level remained low compared to the control even after 15 minutes. It is theorized that at the low RPM, the mixing action was so gentle that dust was not dislodged from a given particle once attached to that particle, even though the water was absorbed into the grain.

This points out that the location of the mixing station, relative to the location where the dust is liberated, can be varied, depending on the violence and the amount of dust which needs to be controlled at the dust liberating site. The data also seems to indicate that the time for absorption of water into the grain is a function of the amount added, and that when approximately 1.0% (about the most that should ever be added) is added to corn, it takes approximately 4 minutes to be absorbed and/or evaporated, whereas for soybeans it is much slower, not being complete even for 15 minutes. Where the material is moved under agitation conditions, the upper limit of 4 minutes between consolidation and dumping should be held.

FIGS. 6-10 show the dust control that is achieved when 1%, 0.5%, 0.25%, 0.125% and 0.06% water respectively is added to corn at different mixer speeds. The data shows that there is generally an optimum time range where effective dust control is achieved. The data also shows that the time range where effective dust control is achieved is dependent on the amount of agitation that occurs during the dust control period.

EXAMPLES FROM FULL SCALE WORK

Tests were conducted during a commercial scale grain handling operation to determine the factors that must be present to control dust by water addition. The tests described herein were conducted while grain was loaded into a ship. However, it is obvious that this invention is not limited to shiploading but is applicable to grain handling operations in general.

Figure 13:
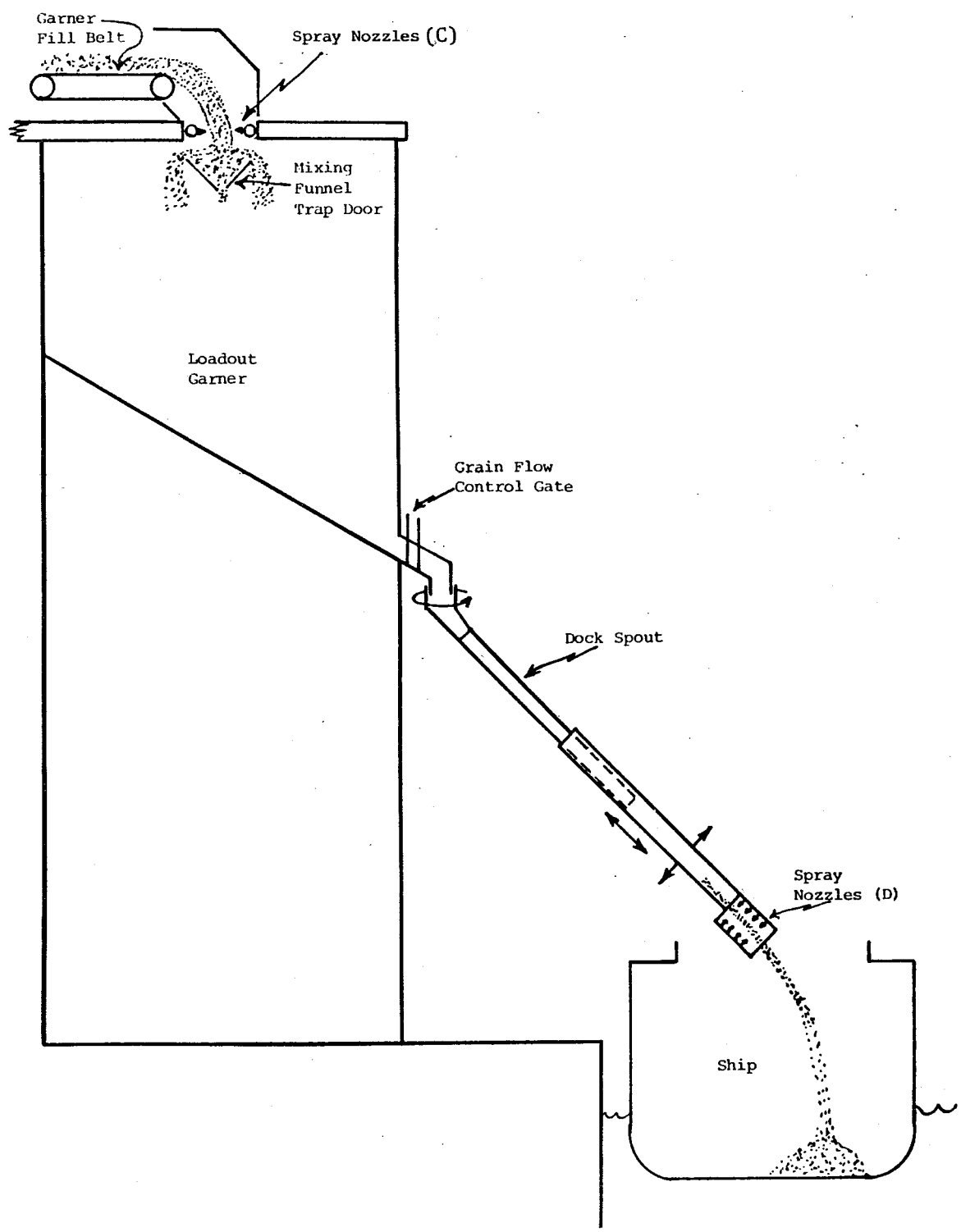
FIG. 13 is a schematic diagram of a ship loading facility which was used to generate the data given in FIG. 14.

The equipment utilized for these tests is illustrated in FIG. 13. Grain was delivered to the load out garner via the garner fill belt. The grain passed by spray nozzles C and through the funnel shaped door at the top of the garner. Said door automatically opened when grain was flowing due to the weight of the grain in the funnel shaped door as grain spilled over the funnel, and the door automatically closed when grain flow was stopped due to the fact that the grain in the funnel trickled out of the funnel through the small hole at the bottom. Said door was installed during the construction of the elevator to help control air flow in the original, conventional dust control system. Said door was not specifically installed for these tests. The grain then passed into the load out garner, through the open grain flow control gate, and directly into the ship. In loading mode A (See FIG. 13), the grain was not held in the garner and all water was applied by the nozzles C.

In loading mode B (See FIG. 13), the grain flow control gate was closed, the garner was filled with grain and the grain was held approximately 15 minutes in the garner prior to opening the grain flow control gate. After the grain flow control gate was opened, the grain passed through the dock spout, and the water was added by spray nozzles D.

Opacity readings were taken during these tests following the standard procedure utilized by the U.S. Environmental Protection Agency for taking these measurements. The results of this series of tests for corn are given in FIG. 14. Test 1 is the control with no liquid added and exhibited an opacity of 31%. Test 2 shows the effect of adding water at the end of the spout (spray nozzles D) which have essentially no dust suppression even at water levels as high as 1%. Test 3 shows the effect of holding grain for an extended period of time (approximately 15 minutes) after adding water. Again, essentially no dust control was observed.

Figure 15:
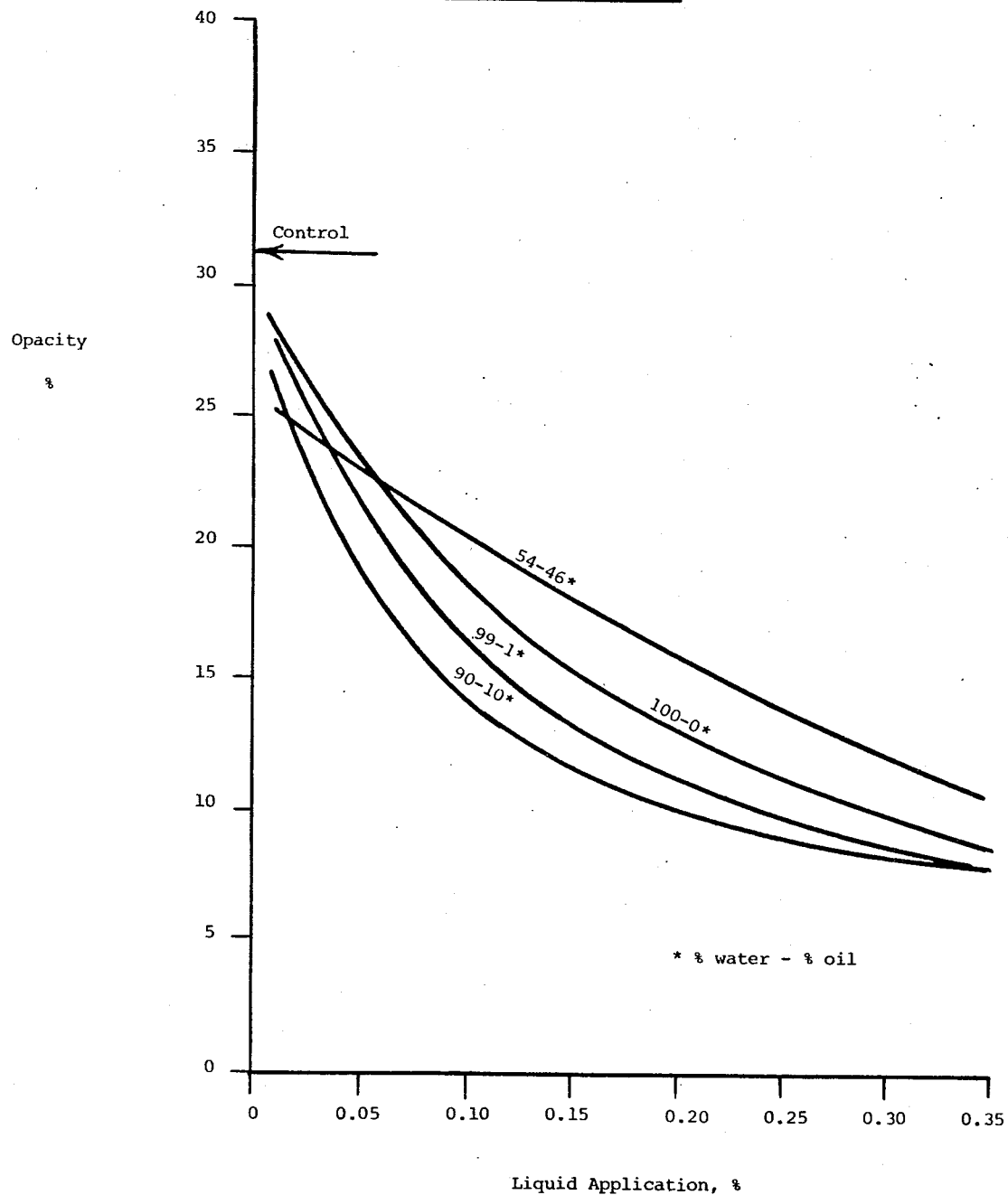
FIG. 15 is a graph of data given in FIG. 14.

Tests 4-33 show the effect of adding various levels of liquid following the invention described herein. As can be seen from FIG. 14, water containing a small amount of emulsifying agent, and various water-oil emulsions were effective in controlling dust. These results are illustrated graphically in FIG. 15. As can be seen in FIG. 15, the oil in water emulsions (those containing 1% and 10% oil) perform slightly better than water, whereas the water in oil emulsion (that containing 46% oil) performed worse than water. It is thus a preferred embodiment of this invention to use oil in water emulsions if an emulsion is the liquid employed. For economic reasons, however, the preferred liquid is normally water. The data indicates that the water added can contain oils and/or impurities.

Subsequent tests have shown that spray nozzles installed just after the grain flow control gate gave slightly better dust control than did the spray nozzles C in loading mode A. These results suggest that unnecessary mixing after water addition had an adverse effect on dust control. The adverse effect of mixing after water addition was confirmed when mixing plows were added in the dock spout and water was added through spray nozzles installed just after the grain flow control gate. However, mixing in the water addition area was found to be beneficial as evidenced by better dust control results when mixing fins were installed in the water addition area.

Although the invention will have particular advantages in controlling the dust that is generated during the handling of grain, applicants do not want others to use the principles hereof with impunity when applied to fertilizers, coal, or other material which may have a dust problem that is similar to that solved by applicants in the handling of grain.

Tests were conducted in the same mixers used above for obtaining the data shown in FIGS. 5 through 10, using the same procedures, excepting that the mixers were charged with various other dusty materials instead of grain. The results of the tests with these materials are given in FIGS. 16 through 19.

Figure 16:
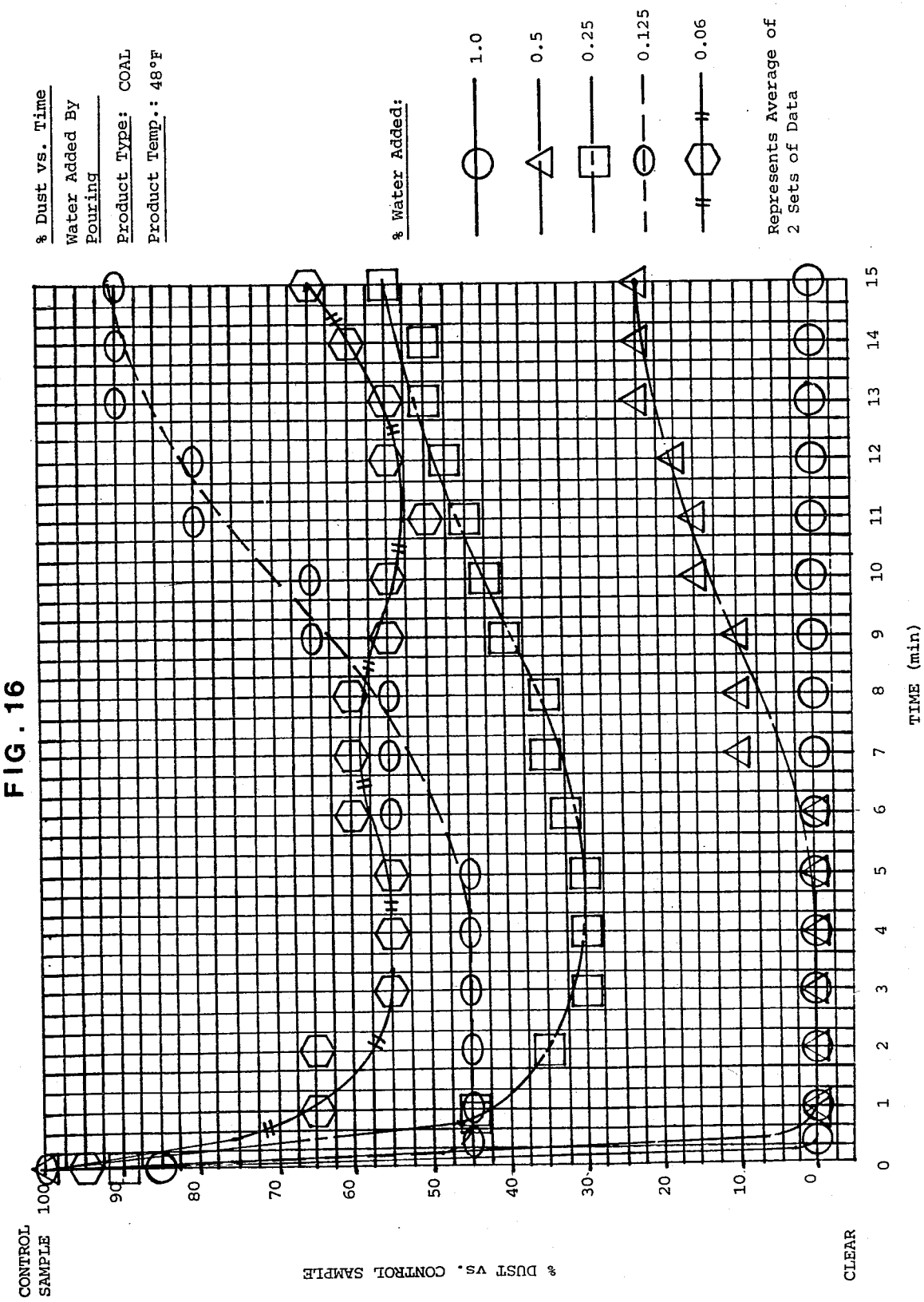
FIG. 16 is a graph showing levels of coal dust achieved when a mixer of FIGS. 11 and 12 was charged with coal and water was poured therein.

The test results shown in FIG. 16 were obtained by charging pea size Pennsylvania anthracite coal to the mixers. There appears to be some experimental error in the results obtained when water in the amount of 0.06% of the weight of the coal was added. Nevertheless, the graph clearly shows the same type of results that were obtained when grain was charged to the mixers. One of the major differences between coal and grain is that coal is much less water absorbing. In other words, water has much less tendency to be absorbed into the pores of coal, than it does in the pores of grain. Comparing FIG. 16 with the 44 RPM curves of FIG. 6 through 10, it will be seen that the same general shape of curve exists, but that the effect of the coal is much longer lasting. Nevertheless, continued agitation causes the dust to be regenerated, apparently after the water is evaporated.

Similar tests were conducted in the mixers on fertilizer grade diammonium phosphate, potash and urea—all of which absorb water better and faster than does coal. The results of these tests are even more interesting. These materials absorb water by a different process than does grain. In grain, water flows into pores and is absorbed like a sponge. With grain the vapor pressure of water is not reduced appreciably since the grain does not go into solution. With solutions, the vapor pressure at the surface decreases as more and more solute goes into solution. Diammonium phosphate, potash, and urea are all soluble in water, with urea being the most soluble. As water is taken into the surface of these materials, it is absorbed by a solvation process. If the amount of water added is small compared to the amount of solute, the surface of the solute particles will have a saturated solution thereon which is either highly ionic or highly polar, and it thus very effectively drains off the charge on dust particles that come in contact therewith. What is more, the vapor pressure of the solution is much lower than that of pure water and therefore evaporation from the surface of the solids is much slower than is evaporation of water from the surface of grain. Comparing the graphs for corn, coal and urea, for example, it will be seen that using the same percent by weight of water, the surpression of dust is shortest on grain, slightly longer with coal and longest lived with urea. It would appear that water on grain is absorbed into its interior much faster than is water on coal; and therefore, the effect of water on grain is shorter lived. With solvatable materials such as urea, the evaporation from its surface is much slower and therefore the effect of the water is longer lasting.

Applicants have now demonstrated that a small amount of water on the surface of solids is much more effective than is water vapor in the air around the solids. Most of the prior art has tried in one way or another to capture or treat the charge on dust particles in the air. Controlling the humidity of the air, as by introducing steam to the air, or by the use of electrostatic precipitators, are examples of techniques for counteracting the charge on particles once they have left the surface of the solid dust producing materials. It now seems clear that applicants have discovered a more effective way of controlling dust—this by controlling the charge of the dust particles while the dust particles are on the surface of the solids being transported.

Figure 17:
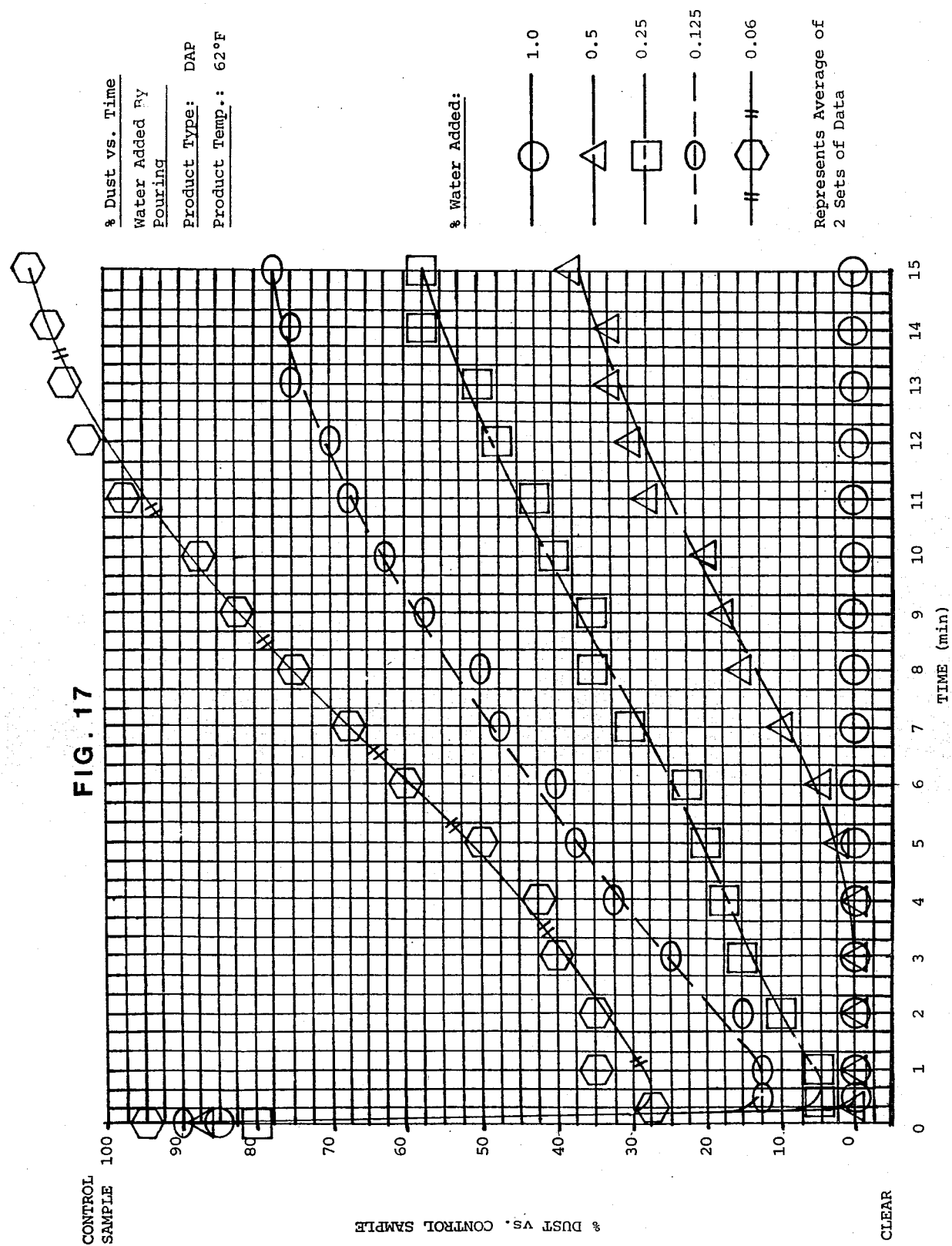
FIG. 17 is a graph showing levels of dust achieved when a mixer of FIGS. 11 and 12 was charged with diammonium phosphate fertilizer, and water was poured therein.
Figure 18:
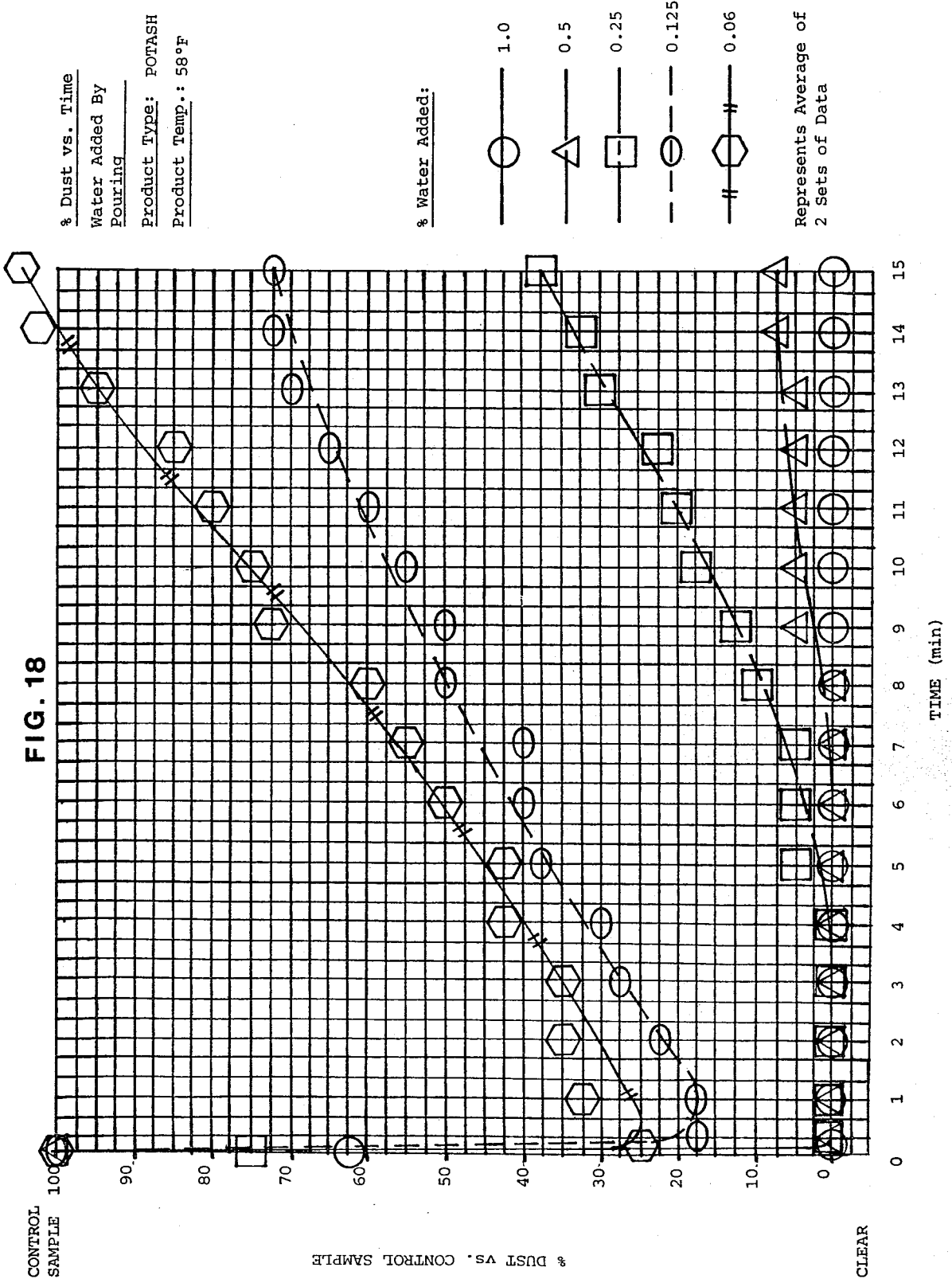
FIG. 18 is a graph showing the levels of fertilizer dust achieved when a mixer of FIGS. 11 and 12 was charged with potash fertilizer and water was poured therein.

With respect to inorganic dusts, FIG. 17 which plots data obtained from diammonium phosphate is believed typical for all ammonium phosphates. It is also believed typical for ammonium nitrates. Ammonium nitrate dusts are very explosive, so that it can be seen that the present invention will not only control ammonium nitrate dust, but in doing so will help to reduce the explosion hazards which occur during its transportation.

Granular water soluble materials tend to cake when wetted, and therefore it is desirable to use only as much water as is necessary to control their dusts. During fall through air, a good deal of the water added will evaporate and thereafter it is desirable to cause the granular material to be gently moved as air circulates over or around the granules following their fall through the air. Such movement will occur by letting the granules slid down a cone shaped pile while the last of the water added is being evaporated. In most cases, 0.5% of added water will overcome the dusting problem, and at the same time will leave too little water remaining after a free fall to create much of a caking problem.

While the invention has been described in considerable detail, we do not wish to be limited to the particular embodiments shown and described, and it is our intention to cover hereby all novel adaptations, modifications and arrangements thereof which come within the practice of those skilled in the art to which the invention relates and which fall within the purview of the following claims.

We claim:

1. A method of reducing the liberation of dust particles from a dry particulate material that is transported in a material stream to a location where it falls through the air, said method comprising: introducing a small amount of water onto contain ones of said particles in said material stream prior to reaching such location, said water being in an amount of at least 0.01% and no more than 1% of the weight of the dry particulate material, causing such wetted particles to constant and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

2. The method of claim 1 wherein said water droplets contain more than 0.5 ppm of chlorine.

3. The method of claim 1 wherein said particles remain in touching engagement for at least 3 seconds.

4. The method of claim 1 wherein the dry particulate material is a perishable organic food.

5. The method of claim 1 wherein said dry particulate perishable food is a whole grain or oilseed.

6. The method of claim 1 wherein said grain is shelled corn kernels.

7. The method of claim 1 wherein said introducing of water onto particles of the grain is accomplished by providing a free fall to the grain particles and introducing a spray of water droplets onto the stream of free falling grain.

8. A method of reducing the liberation of dust particles from a dry particulate perishable food that is transported in a material stream to a discharge location where it falls through the air, said method comprising: introducing a small amount of water onto certain ones of said particles in said material stream prior to reaching such location, said water being in an amount of at least 0.01% and no more than 1% of the weight of the dry particulate material, causing such wetted particles to contact and be distributed throughout the remainder of the material stream prior to reaching such discharge location, delaying the delivery of the wetted particles by a period of at least one second prior to reaching such location, and providing a smooth path for the particle stream after such distribution and prior to discharge at such location, whereby agitation of the material stream is minimized after such distribution and prior to discharge.

9. The method of claim 8 wherein the water added contains at least 0.5 ppm of chlorine.

10. The method of claim 8 wherein said dry particulate perishable food is a whole grain or oilseed.

11. A method of reducing the escape of dust from a stream of grain that slides down a spout to fall from the end thereof, said method comprising: causing the grain which slides down said spout to mix at a location following which it takes the stream a second or more to reach the end of the spout, spraying water droplets onto the grain at said location, said droplets comprising from 0.01% to 1% of the weight of the grain, and causing the grain particles of the stream to be consolidated for at least a second before reaching the end of the spout.

12. The method of claim 11 wherein said water droplets contain at least 0.5 ppm of chlorine.

13. The method of claim 11 wherein said mixing is part of a free fall during which water is sprayed on the falling particles.

14. The method of claim 11 wherein said time to reach the end of the spout is at least 3 seconds.

15. The method of claim 11 wherein said particulate material is a whole grain or oilseed.

16. A method of reducing the liberation of dust particles from coal that is transported in a material stream to a location wherein it falls through air, said method comprising: introducing a small amount of water onto certain ones of said particles in said material stream prior to reaching such location, said water being in an amount of at least 0.25% and no more than 1% of the weight of the dry particulate material, causing such wetted particles to contact and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

17. The method of claim 16 wherein the amount of water introduced is approximately 0.5% of the weight of the coal.

18. A method of reducing the liberation of dust particles from an ammonium phosphate granular material that is transported to a location wherein it falls through air, said method comprising: introducing a small amount of water onto certain ones of said particles in said material stream prior to reaching such location, said water being in the amount of at least 0.125% and no more than 1% of the weight of the dry particulate material, causing such wetted particles to contact and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

19. The method of claim 18 wherein the amount of water introduced is from approximately 0.125% to approximately 0.5% of the weight of the ammonium phosphate material.

20. A method of reducing the liberation of dust particles from granular potash that is transported to a location wherein it falls through air, said method comprising: introducing a small amount of water onto certain ones of said particles in said material stream prior to reaching such location, said water being in the amount of at least 0.125% and no more than 1% of the weight of the dry particulate material, causing such wetted particles to contact and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

21. The method of claim 20 wherein the amount of water introduced is from approximately 0.25% to approximately 0.5%.

22. A method of reducing the liberation of dust particles from an ammonium nitrate granular material that is transported to a location wherein it falls through air, said method comprising: introducing a small amount of water onto certain ones of said particles in said material stream prior to reaching such location, said water being in the amount of at least 0.125% and no more than 1% of the weight of the dry particulate material, causing such wetted particles to contact and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

23. The method of claim 22 wherein the amount of water introduced is from approximately 0.25% to approximately 0.5%.

24. A method of reducing the liberation of dust particles from granular urea that is transported to a location wherein it falls through air, said method comprising: introducing a small amount of water onto certain ones of said particles in said material stream prior to reaching such location, said water being in the amount of at least 0.069% and no more than 1% of the weight of the dry particulate material, causing such wetted particles to contact and be distributed generally uniformly throughout the remainder of the material prior to reaching such location, delaying the delivering of the wetted particles by a period of at least one second prior to reaching such location, and providing a smooth path for the material stream after such uniform distribution and prior to discharge at such location, whereby agitation of the material stream is minimized after such uniform distribution and prior to discharge.

* * * * *

UNITED STATES PATENT AND TRADEMARK OFFICE
CERTIFICATE OF CORRECTION

PATENT NO. : 4,439,211
DATED : March 27, 1984
INVENTOR(S) : Donald E. Anderson et al.

It is certified that error appears in the above-identified patent and that said Letters Patent is hereby corrected as shown below:

Column 9, line 1, "contain" should read -- certain --.

Signed and Sealed this

Fourth Day of December 1984

[SEAL]

Attest:

GERALD J. MOSSINGHOFF

Attesting Officer    Commissioner of Patents and Trademarks